(12) United States Patent
Müller

(10) Patent No.: US 9,962,190 B2
(45) Date of Patent: May 8, 2018

(54) MTV IMPLANTATION SET

(71) Applicant: Friedrich Müller, Lüneburg (DE)

(72) Inventor: Friedrich Müller, Lüneburg (DE)

( * ) Notice: Subject to any disclaimer, the term of this patent is extended or adjusted under 35 U.S.C. 154(b) by 259 days.

(21) Appl. No.: 14/760,312

(22) PCT Filed: Jan. 15, 2013

(86) PCT No.: PCT/EP2013/050682
§ 371 (c)(1),
(2) Date: Jul. 10, 2015

(87) PCT Pub. No.: WO2014/111134
PCT Pub. Date: Jul. 24, 2014

(65) Prior Publication Data
US 2016/0000469 A1     Jan. 7, 2016

(51) Int. Cl.
| | | |
|---|---|---|
| *A61B 17/70* | (2006.01) | |
| *A61B 17/84* | (2006.01) | |
| *A61B 17/88* | (2006.01) | |
| *A61B 17/17* | (2006.01) | |
| *A61B 17/16* | (2006.01) | |
| *A61B 90/00* | (2016.01) | |

(52) U.S. Cl.
CPC ........ *A61B 17/7032* (2013.01); *A61B 17/162* (2013.01); *A61B 17/1757* (2013.01); *A61B 17/846* (2013.01); *A61B 17/8888* (2013.01); *A61B 17/1615* (2013.01); *A61B 17/1664* (2013.01); *A61B 17/1671* (2013.01); *A61B 17/848* (2013.01); *A61B 2090/034* (2016.02)

(58) Field of Classification Search
CPC ... A61B 17/84; A61B 17/683; A61B 17/7055; A61B 17/846; A61B 17/86; A61B 17/8605; A61B 17/862; A61B 17/863; A61B 17/864; A61B 17/8888; A61B 17/8897
See application file for complete search history.

(56) References Cited

U.S. PATENT DOCUMENTS

| | | | | |
|---|---|---|---|---|
| 5,129,901 A * | 7/1992 | Decoste | ............... | A61B 17/742 606/304 |
| 5,529,075 A * | 6/1996 | Clark | ............... | A61B 17/68 128/898 |
| 6,635,059 B2 * | 10/2003 | Randall | ............... | A61B 17/683 606/304 |
| 2002/0087161 A1 * | 7/2002 | Randall | ............... | A61B 17/683 606/916 |

(Continued)

OTHER PUBLICATIONS

European Patent Office, Rijswijk, Netherlands, Translation of International Search Report of International Application No. PCT/EP2013/050682, dated Jul. 5, 2013.

*Primary Examiner* — Jacqueline Johanas
(74) *Attorney, Agent, or Firm* — Brinks Gilson & Lione

(57) ABSTRACT

An orthopedic implant (3) has permanent attachment to bones in the bodies of vertebrates and/or humans. In particular, the orthopedic implant comprises an elongate, substantially cylindrical base body (15), which can be inserted into patients using minimally invasive treatment together with little trauma to the surrounding tissue. The implant may comprise an external fixing thread (11) for screwing into the bone to sustainably improve treatment outcomes and recovery time.

10 Claims, 8 Drawing Sheets

(56) References Cited

U.S. PATENT DOCUMENTS

| | | | |
|---|---|---|---|
| 2003/0135212 A1* | 7/2003 | Y. Chow | A61B 17/72 606/64 |
| 2008/0234752 A1* | 9/2008 | Dahners | A61B 17/8047 606/291 |
| 2009/0198289 A1* | 8/2009 | Manderson | A61B 17/864 606/304 |
| 2010/0114315 A1* | 5/2010 | Manderson | A61B 17/7225 623/16.11 |
| 2010/0198276 A1* | 8/2010 | Krebs | A61B 17/7266 606/86 R |
| 2010/0268285 A1* | 10/2010 | Tipirneni | A61B 17/742 606/309 |
| 2011/0087296 A1 | 4/2011 | Reiley et al. | |
| 2011/0118792 A1 | 5/2011 | Orsak | |
| 2011/0270312 A1* | 11/2011 | Assell | A61B 17/025 606/256 |
| 2011/0288598 A1* | 11/2011 | Moed | A61B 17/8625 606/303 |
| 2011/0295252 A1* | 12/2011 | Tipirneni | A61B 17/685 606/62 |
| 2011/0301653 A1* | 12/2011 | Reed | A61B 17/1604 606/319 |
| 2011/0313473 A1* | 12/2011 | Prandi | A61B 17/863 606/315 |
| 2012/0323285 A1* | 12/2012 | Assell | A61B 17/8625 606/305 |
| 2013/0013000 A1* | 1/2013 | Ainsworth | A61B 17/70 606/279 |
| 2013/0079776 A1 | 3/2013 | Stewart | |
| 2014/0025117 A1* | 1/2014 | Assell | A61B 17/025 606/258 |

* cited by examiner

MTV IMPLANTATION SET

TECHNICAL FIELD OF THE INVENTION

The present invention relates to an orthopedic implant for permanent attachment to bones in the bodies of vertebrates and/or humans, in particular in order to block vertebrae thereby, comprising an elongate, substantially cylindrical base body.

The present invention further relates to a guide device for pilot-drilling a substantially cylindrical channel in the bone in the bodies of vertebrates and/or humans.

Lastly, the present invention relates to a set comprising at least one implant, at least one guide device, at least one counter means and at least one connection means comprising a portion for establishing an operative connection to a drilling device.

BACKGROUND OF THE INVENTION

An orthopedic implant of the type mentioned at the outset may, in a known manner and in the simplest case, be what is known as a Steinmann pin. Using this, for example in neurosurgery, particularly in veterinary medicine, what is known as cauda equina syndrome (CES), degenerative lumbosacral stenosis (DLSS) or the effects of degenerative discopathy between the lumbar spine and the sacrum can be treated. According to an operative method developed by the inventor of the present invention, by means of a generic implant, that is to say conventionally using a Steinmann pin, in many cases vertebral blocking can be carried out in a minimally invasive manner and as an outpatient, that is to say in particular without large incisions into tissue such as skin, muscle or bone. In this process, the blocking prevents the last lumbar vertebra from sliding back and forth, which is known as subluxation, and therefore prevents the nerve from becoming trapped. In addition, by means of the blocking, pressure on the spinal disc can be relieved, and protrusions or prolapses which already exist can be reduced. In principle, during transiliac vertebral blocking, the known Steinmann pin is guided in particular laterally through the hip bone in order to achieve the desired blocking.

When using Steinmann pins for the above-mentioned purpose, according to the prior art it is, however, disadvantageously necessary to bend the implant, that is to say the Steinmann pin, in a suitable manner directly at the operating site, that is to say to the patient's bone, during the operation and to shorten said implant at the site in a suitable manner in order to fix the implant in the body. Both the process of bending the pin and the process of shortening the pin during the operation in the body are, however, disadvantageously problematic. These processes often lead to undesired trauma of the surrounding tissue and can, in adverse cases, also significantly impede the recovery process.

SUMMARY OF THE INVENTION

In this context, the problem addressed by the present invention is to provide an orthopedic implant of the type mentioned at the outset which can be inserted into patients using minimally invasive treatment together with little trauma to the surrounding tissue, in order to sustainably improve treatment outcomes and recovery times.

With respect to the guide device mentioned at the outset, the counter means, the connection means and the set, the objective is to provide means which facilitate minimally invasive treatment in combination with the orthopedic implant according to the invention in the above-mentioned sense.

With reference to the orthopedic implant for permanent attachment to bones in the bodies of vertebrates and/or humans, in particular in order to block vertebrae thereby, comprising an elongate, substantially cylindrical base body, this problem is solved in that the implant according to the invention comprises an external fixing thread for insertion into the bone. Fixing the implant in the bone by means of a thread has the advantage of it not being necessary to bend the implant in vivo in order to produce blocking, which prevents the last lumbar vertebra from sliding back and forth.

In an advantageous embodiment of the implant according to the invention, the external fixing thread has two complete turns. This embodiment makes it possible to securely and permanently attach the implant to the bone.

In particular, it is advantageous according to the invention for the external fixing thread to have a greater diameter than the base body and/or for the external fixing thread to be formed in a portion of the base body which is widened in the manner of a bead. In this case, the external fixing thread has, according to the invention, a greater diameter than the cylindrical base body of the implant according to the invention. As a result, it is for example possible to arrange the external fixing thread close to an end portion of the cylindrical base body in order to fix the implant according to the invention to the hip bone and, moreover, to insert the relatively thin, cylindrical base body through the hip bone.

In the context of another aspect of the invention, it is also advantageous, in the case of the implant according to the invention, for the base body to be provided at a distal end with distal attachment means, in particular a distal internal thread, in order to releasably attach a guide device so as to extend the base body. In this way, in a manner which is more or less comparable with certain procedures used in tunnel construction, a desired hole can be made in the bone in one continuous processing step, into which hole the implant is automatically inserted when the guide device is advanced because said device is attached to the implant.

Furthermore, it is advantageous according to a further aspect of the invention, in an embodiment of the invention, for said implant to be provided at a proximal end with proximal attachment means, in particular a proximal internal thread, in order to releasably attach connection means which are formed in order to establish an operative connection to a drilling device. In this context, the terms "distal end" and "proximal end" refer to the advancement direction when inserting the implant into the body. The releasable nature of the connection is crucial here, since this makes it possible to remove the guide device, for example by loosening a thread, so that the implant can remain in the body at a pre-assembled length after it has been inserted.

Furthermore, it is provided in a preferred embodiment of the implant according to the invention that said implant is provided at a proximal end with proximal attachment means, in particular a proximal internal thread, in order to releasably attach connection means which are formed in order to establish an operative connection to a drilling device. Here, too, the releasable connection of the implant is advantageously made possible by using a drill attachment having a standardized AO shaft, i.e. a shaft according to the AO standard established by Arbeitsgemeinschaft für Osteosynthesefragen (AO, Working Group for Osteosynthesis Questions), for example. Said attachment can be used in standard drill chucks in order to insert the implant at the desired point and to anchor it in the bone. Once the desired position of the implant in the bone is reached, the connection means can be released from the implant. In the simplest case, this takes place by said means simply being unscrewed. This is also advantageous in that the implant can be pre-assembled to the length desired for achieving the medical effect and a releasable drill attachment having an AO shaft can be used for the insertion process, which attachment only effectively lengthens the implant during the insertion process in order for it to be screwed in from outside the body.

In an advantageous embodiment of the implant according to the invention, it is provided that the base body comprises at least one counter portion having a non-circular cross-sectional profile, which portion is preferably arranged between the external fixing thread and the proximal end. In order to keep trauma to the surrounding tissue to a minimum, and in order for there to be no further change in the position of an implant which is fixed in a desired position in the bone by means of the external fixing thread, using the counter portion it can be ensured that, when removing the guide device and/or the connection means for the drilling device, no torque is transmitted to the implant when the screwed connections are being released, for example. The counter portion according to the invention may for example be in the form of a hexagon nut, and/or in that the periphery of the implant in the region of the counter portion is in the form of a hexagon nut.

In order to ensure that no trauma to the tissue is caused by the countering when using the counter portion to remove the guide device and/or the connection means for the drill, in an embodiment of the implant according to the invention it is provided that the base body comprises a conical portion which is connected to the counter portion, preferably in the direction of the distal end, projects radially beyond said portion at the end facing said portion and tapers, preferably towards the distal end. The base of the conical portion functions here as a contact surface, whereas the conical portion ensures as smooth a transition as possible in the direction of the bone and the screwed connection.

In an embodiment of the invention, the distal internal thread and the proximal internal thread of the implant have a corresponding rotational direction. For example, a standard right-handed thread may be used. If the implant according to the invention is provided with a counter portion, for example a hexagon nut, the screwed connection can in any case be released after the implant has reached the desired position in the bone, without further torques being transmitted to the implant. Therefore, an embodiment in which the thread is in the opposite direction is for example also not necessary for keeping the implant free of torque.

With respect to the guide device of the invention for pilot-drilling a substantially cylindrical channel in bones in bodies of vertebrates and/or humans, the problem mentioned at the outset is solved in that the guide device is designed to be releasably attached so as to extend the base body of an implant by cooperating with the distal attachment means, the guide device comprising at least one counter portion, which has a non-circular cross-sectional profile. In the context of the invention, the counter portion may be designed as a square portion, using which, in the case of a countered implant, the guide device can be released, for example unscrewed, from the implant using a corresponding square wrench.

In an embodiment of the invention, the guide device preferably has, on a proximal end, an external thread which is complementary to the distal internal thread of the implant. In this way, the guide device, which may for example be designed as a guide pin, can advantageously be screwed to the implant before said implant is inserted.

If, in an embodiment of the guide device according to the invention, a distal end is formed in tapered manner, preferably in the manner of a right pyramid, comprising edges which are formed for cutting and/or drilling bones, the guide device can be used in the manner of a drill, which pulls the implant into the hole produced while the hole is being made when the implant is screwed to the guide pin which is designed in this way. The specific form of the end in the manner of a pyramid has proven to be advantageous according to the invention in terms of minimizing trauma to the adjacent tissue.

With respect to the counter means of the above-mentioned type, the above problem is solved according to the invention by a counter means of this type which is used to transmit a torque to the implant and with a direction vector parallel to the longitudinal axis of the implant, and comprises a counter-means-side counter portion which has a cross-sectional profile which is formed so as to be complementary to the cross-sectional profile of the implant-side counter portion. If the implant-side counter portion is formed in the manner of a hexagon nut, according to the invention the counter-means-side counter portion is for example designed as an open-end wrench or as a socket wrench having a hexagon-socket profile. In this way, the counter means can be designed as a hexagon wrench, which makes it possible for any torques acting on the implant to be compensated when releasing or attaching components from/to the implant by establishing or disconnecting a screwed connection. The implant thus advantageously does not rotate in an undesired manner.

In a development of the invention, the counter means may be formed as a hollow cylinder to be placed over the counter portion of the base body of the implant. This embodiment also makes it possible to guide a drill attachment comprising a standard AO shaft through the counter means, in order to be able to release components from the implant or attach them thereto without torque being transmitted to the implant in an undesired manner.

Insofar as the invention is directed to connection means of the type mentioned at the outset, the problem addressed is solved in that the connection means comprise, at a distal end, means for releasable attachment to an implant, preferably an external thread which is complementary to the proximal internal thread of the implant, and are preferably designed to carry out by means of a counter means. In particular, the connection means may be designed as a drill attachment comprising an AO shaft, which also comprises a stop.

Similarly, the problem directed to a connection means is solved by said means comprising, at a distal end, means for attachment to a guide device, preferably an internal thread which is complementary to the external thread of the guide device, and comprising at least one counter portion having a non-circular cross-sectional profile. A connection means formed in this way makes it possible, according to the invention, to connect the guide device, that is to say for example the guide pin, directly to the drilling device when pilot-drilling for the final implant according to the invention, without the actual implant already having to be used in this phase of the operation.

Lastly, the problem directed to a set of the type mentioned at the outset is solved in that at least one implant is designed to cooperate with at least one of the guide devices, at least one of the counter means and at least one of the connection means. In practice, a set may comprise a plurality of implants of different lengths, which are each suitable for different patients and clinical pictures, which implants can in turn cooperate with different guide devices. For example, guide pins of different thicknesses which are compatible with the thickness of the implant in question may be used, for which thicknesses said guide pin is intended to bring about pilot-drilling.

If, according to the invention, the set additionally contains connection means, in the first pilot-drilling step a connection between the guide device, that is to say the guide pin for example, and the drilling device can be directly made, without the implant having to be installed.

The invention is described by way of example in a preferred embodiment with reference to the drawings, further advantageous details emerging from the figures of the drawings. The drawings are provided for purely illustrative purposes and are not intended to limit the scope of the present invention.

Functionally like parts are provided with the same reference numerals in the drawings.

DETAILED DESCRIPTION OF THE DRAWINGS

Figure 1:
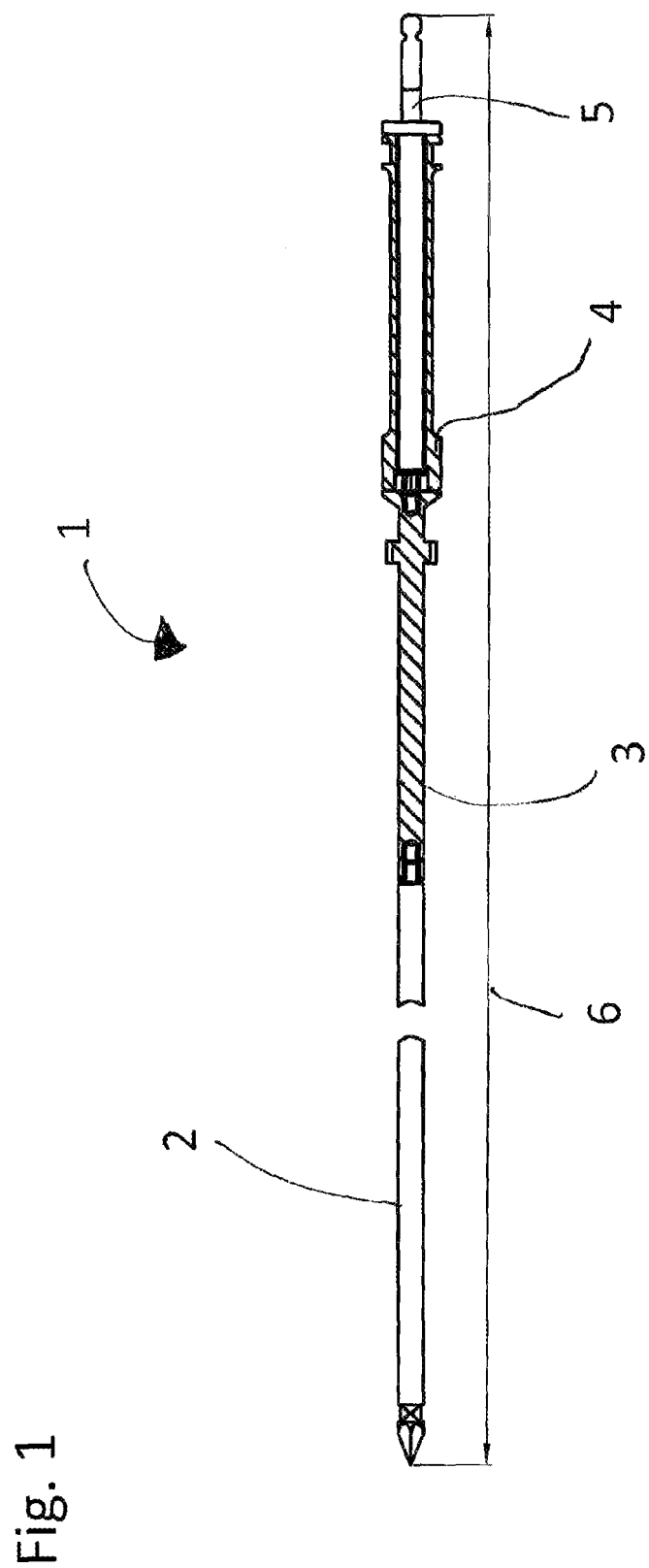
FIG. 1 is a side view in partial axial section of a tool according to the invention for fitting the implant, consisting of a guide pin according to the invention, an MTV implant, a socket wrench fitted onto the MTV implant, and a drill mount which is guided through the socket wrench and is screwed to the MTV implant.

FIG. 1 is a side view in the radial viewing direction of an assembled tool 1 according to the invention for fitting the implant. The assembled tool 1 consists, at the distal end, of a guide device in the form of a guide pin 2. The guide pin is described in greater detail below in conjunction with FIG. 3. The guide pin 2 is screwed, at the proximal end, to an MTV implant 3 according to the invention for minimally invasive transiliac vertebral blocking (MTV). The MTV implant 3 according to the invention is described in greater detail below in conjunction with FIG. 2. A socket wrench 4 according to the invention is fitted onto the proximal end of the MTV implant 3 as a counter means. The socket wrench 4 is described in greater detail below in conjunction with FIG. 4. A drill attachment 5 comprising an AO shaft is guided through the socket wrench 4 and is screwed to the MTV implant 3. The drill attachment 5 is described in greater detail below in conjunction with FIG. 5.

The assembled tool 1 for fitting the implant has a total length 6 which is sufficient for the assembled tool 1 to be inserted through the body such that at least the distal end of the guide pin 2 and the proximal end of the socket wrench 4 are positioned outside the body when the MTV implant 3 is fixed in the body at the desired installation site.

Figure 2:
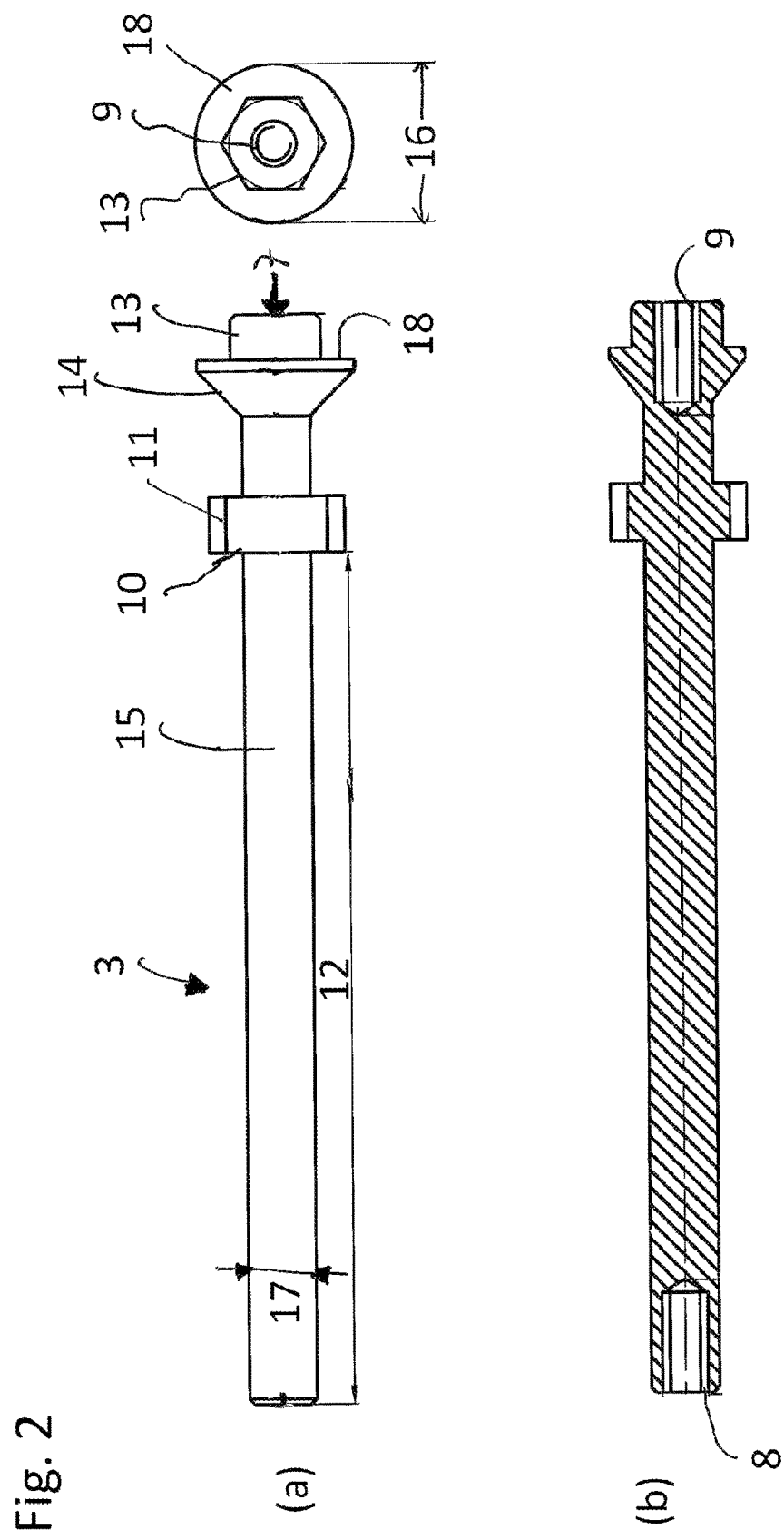
FIG. 2 separately shows two views, namely a longitudinal side view (a) and an axial section (b), of the MTV implant according to the invention from the assembled tool according to FIG. 1.

FIG. 2 separately shows the MTV implant 3 according to the invention as a core element of the assembled tool 1 for fitting the implant according to FIG. 1. In this case, part (a) of the figure shows a side view in the radial viewing direction and, to the right thereof, a view in the axial direction in the direction of the arrow 7. Part (b) of FIG. 2 is an axial section through the MTV implant 3. The MTV implant 3 comprises, at the distal end, an axial hole having an internal thread 8 for receiving the guide pin 2. At the proximal end, an axial hole having an internal thread 9 is formed in order to screw in the drill attachment. Both the internal thread 8 and the internal thread 9 are standard right-handed threads. Close to the proximal end, the MTV implant 3 has a bead-like widening 10 having an external fixing thread 11. The external fixing thread 11 is specially designed for fixing into bones and has two complete turns.

The region between the bead-like widening 10 and the distal end of the MTV implant defines a pin length 12 which, depending on the requirements of the operative intervention, can be suitably selected. For example, the pin length may be 12 75 mm. As can be seen particularly well in the plan view in the right-hand side of FIG. 2(a), the proximal end of the MTV implant 3 is formed as hexagon nut 13, through which the hole having the internal thread 9 is guided. In the axial direction towards the distal end of the MTV implant 3, the hexagon nut 13 adjoins a conical portion 14. The conical portion 14 projects beyond the cylindrical base body 15 of the MTV implant 3 on the side facing the hexagon nut 13, since the diameter 16 of the conical portion 14 is greater here than the diameter 17 of the cylindrical base body 15 of the MTV implant 3. In this way, a contact surface 18 is produced which axially adjoins the hexagon nut 13. The MTV implant 3 consists of stainless steel, in particular according to the standard 1.4571, and is formed in one piece.

Figure 3:
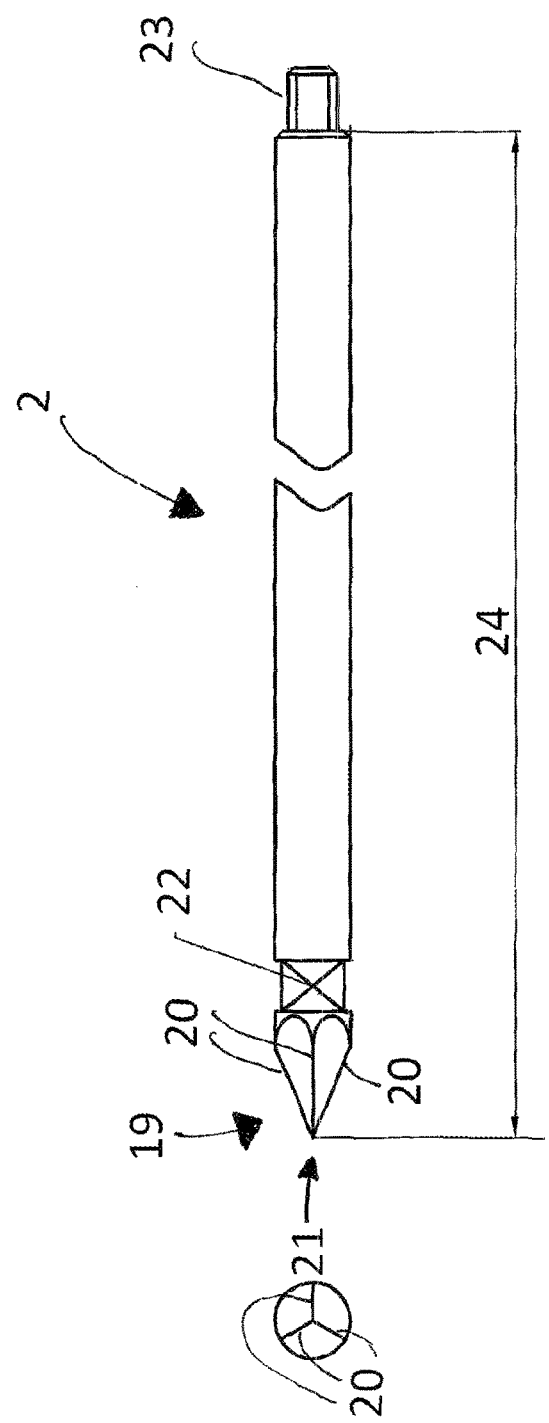
FIG. 3 separately shows a side view in the radial direction of the guide pin according to the invention as a component of the assembled tool shown in FIG. 1.

FIG. 3 separately shows the guide pin 2 of the assembled tool 1 for fitting the implant according to FIG. 1. In the guide pin 2 according to the invention, the distal end 19 is formed in tapered manner in the manner of a right pyramid, comprising edges 20 which are formed for cutting and/or drilling bones. This can also be seen from the direction of the arrow 21 in the axial plan view shown on the left in FIG. 3. In the axial direction, a square portion 22 is connected to the distal end 19 of the guide pin 2. An external thread 23 which is compatible with the internal thread 8 of the MTV implant 3 is located on the proximal end of the guide pin 2. The free total length 24 of the guide pin 2 according to the invention when it is screwed to the MTV implant 3 is selected such that at least the square portion 22 is outside the body when the MTV implant 3 has reached the desired position in the patient's bone.

Figure 4:
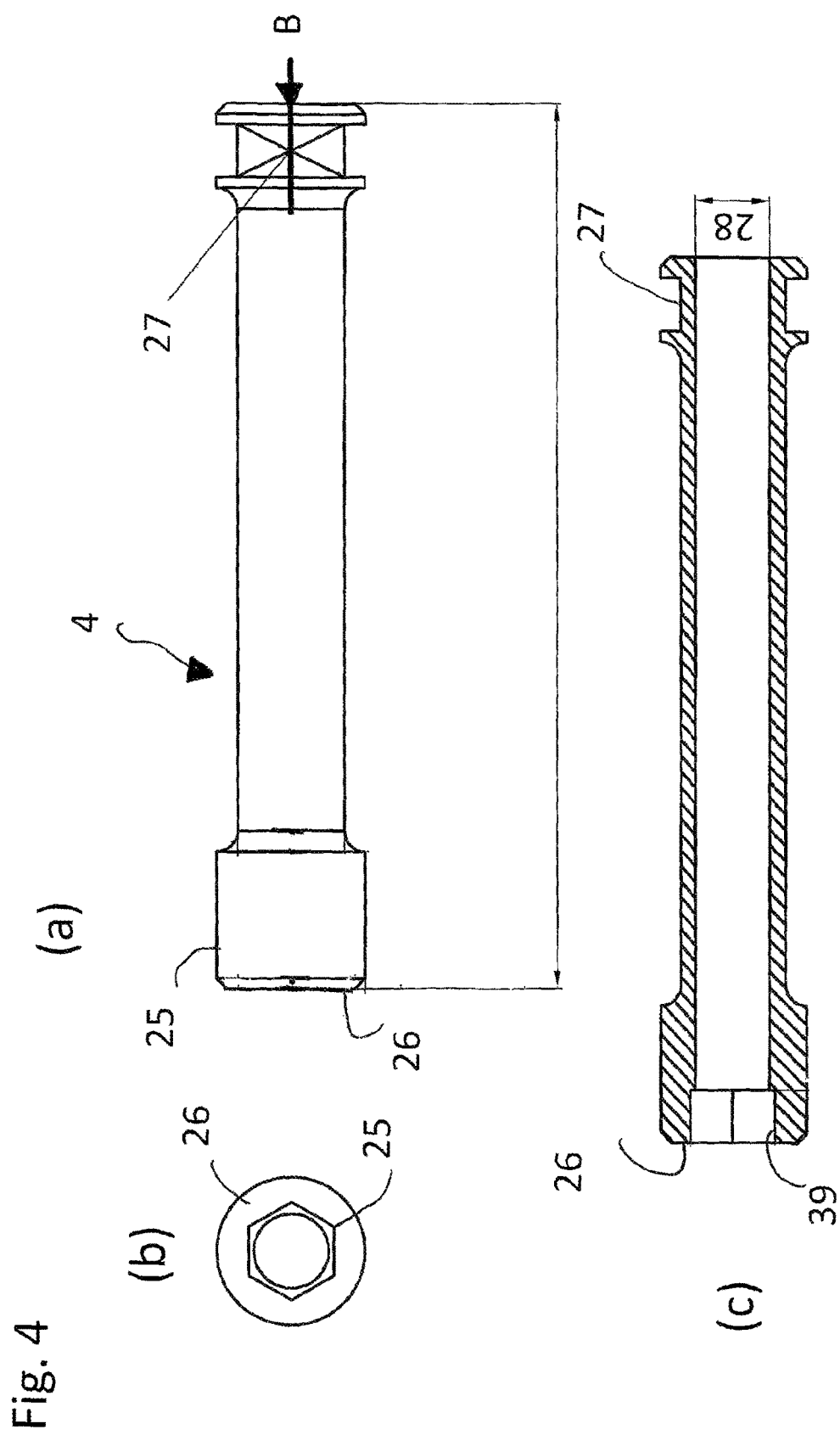
FIG. 4 separately shows three views, namely a side view in the radial direction in FIG. 4(a), an axial plan view in the direction of the arrow B in FIG. 4(b), and an axial section in FIG. 4(c), of the socket wrench shown in FIG. 1 as a component of the assembled tool shown in said figure, as a counter means according to the invention.

FIG. 4 separately shows various views of the socket wrench 4 of the assembled tool 1 from FIG. 1. As can be seen from the axial section according to FIG. 4(c), the socket wrench 4 is formed substantially as a hollow cylinder. Here, the diameter 38 of the central hole in the socket wrench 4 is selected such that the drill attachment 5 can be inserted through the socket wrench 4 and can be rotated therein relative to the socket wrench 4. On the distal end of the socket wrench 4, a hexagon-socket profile 39 is formed with the central hole and is designed to cooperate with the hexagon nut 13 on the MTV implant 3 side. In addition, a bead 25 having a relatively large outer diameter is arranged in the distal region of the socket wrench 4, which bead leads to the end face 26 having a diameter on the distal end of the socket wrench 4 which approximately corresponds to that of the contact surface 18 of the conical portion 14 of the MTV implant 3. In this way, the distal end of the socket wrench 4 is suitable for being fitted onto the hexagon nut 13 on the proximal end of the MTV implant 3 until the end face 26 of the socket wrench 4 is in contact with the contact face 18 of the MTV implant 3.

Figure 5:
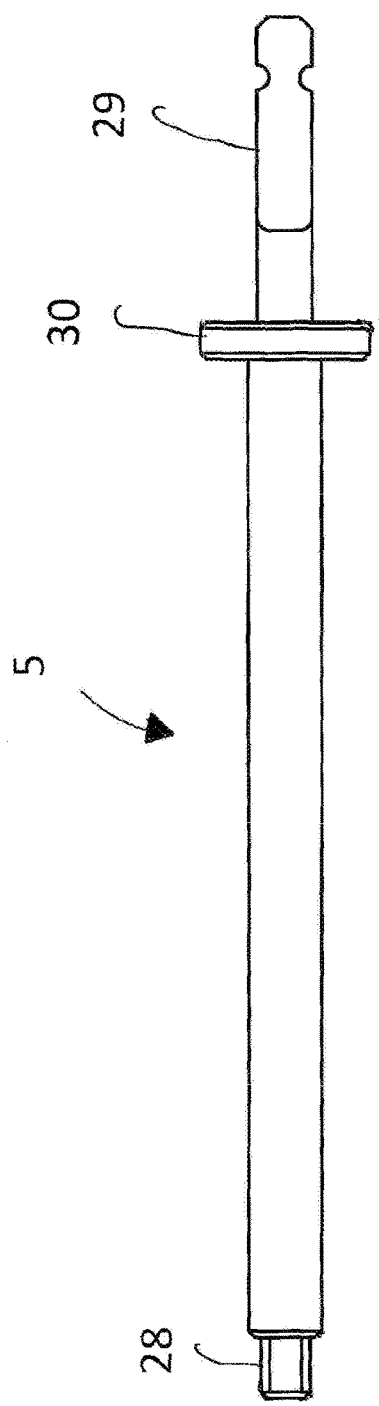
FIG. 5 separately shows a radial side view of the drill mount of the assembled tool shown in FIG. 1 as an embodiment of the connection means according to the invention.

On the proximal end of the socket wrench 4, said socket wrench 4 has a square outer profile 27 in order for a counter wrench to be placed thereon. FIG. 5 separately shows the drill attachment 5 of the tool 1 shown in FIG. 1 for fitting the implant. The distal end of the drill attachment 5 has an external thread 28 in order for it to be screwed into the internal thread 9 in the MTV implant 3. The proximal end of the drill attachment 5 comprises an AO shaft 29 in order to connect it to a standard drilling device. The AO shaft 29 comprises a stop 30 towards the distal end of the drill attachment 5 in the axial direction, the outer diameter of which stop is adapted such that it can be placed onto the proximal end face of the socket wrench 4.

Figure 6:
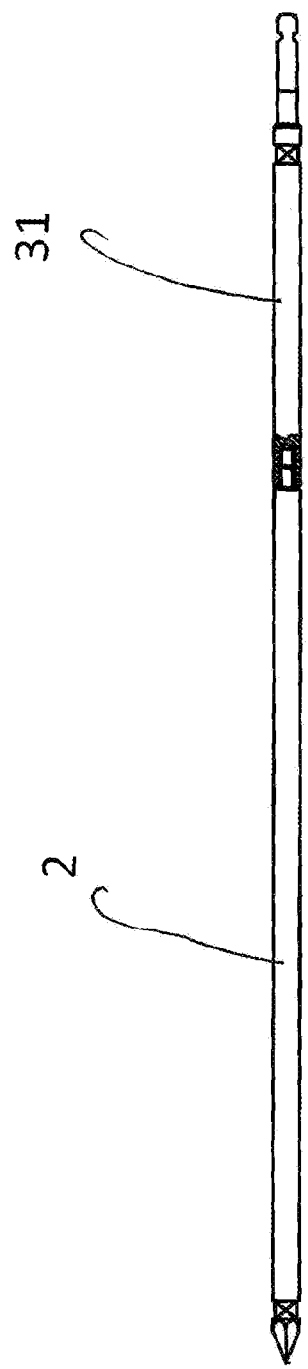
FIG. 6 shows another embodiment of the assembled tool according to the invention, consisting of a guide pin according to the invention as a preferred configuration of a guide device according to the invention, which pin is screwed to a drill mount according to the invention as a preferred configuration of the stop means according to the invention.

FIG. 6 shows another assembled tool consisting of the guide pin 4 according to the invention from FIG. 4 and a drill attachment 31. The drill attachment is screwed to the socket wrench 4.

Figure 7:
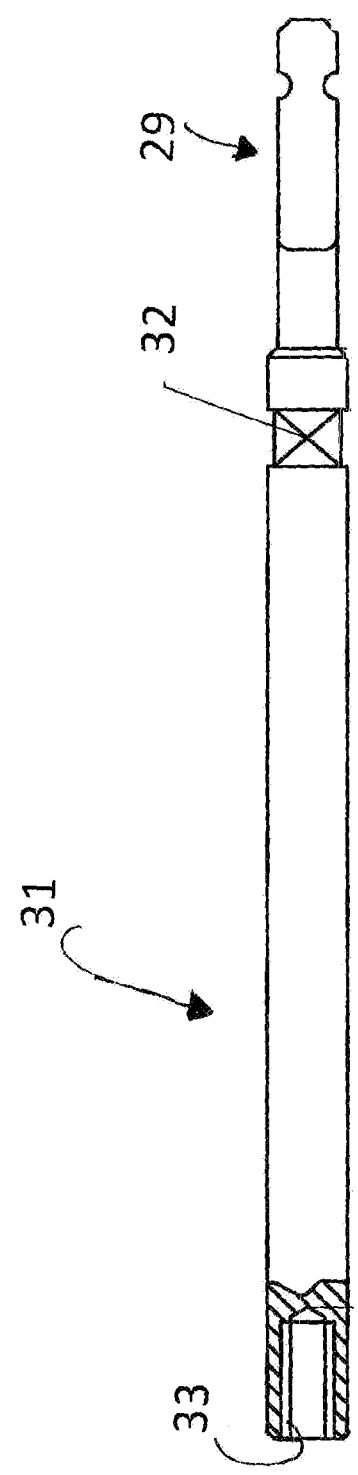
FIG. 7 separately shows a radial side view in partial axial section of the drill mount according to the invention of the assembled tool according to FIG. 6.

As can be seen from FIG. 7, which separately shows the drill attachment 31, said attachment comprises an AO shaft 29 at the proximal end for chucking a standard drilling device. This may be carried out in particular by means of a drill chuck. In the axial direction towards the distal end of the drill attachment 31, the drill attachment 31 has a square outer profile 32 in order for it to be fitted to a counter wrench. By contrast with the drill attachment 5 according to FIG. 5, which is inserted in the case of the assembled tool 1 according to FIG. 1, the distal end of the drill attachment 31 comprises an axial hole having an internal thread 33. The internal thread 33 is selected so as to be compatible with the external thread 23 of the guide pin 2 in order for the drill attachment 31 to be screwed to the guide pin 2 to produce the tool shown in FIG. 6.

Figure 8:
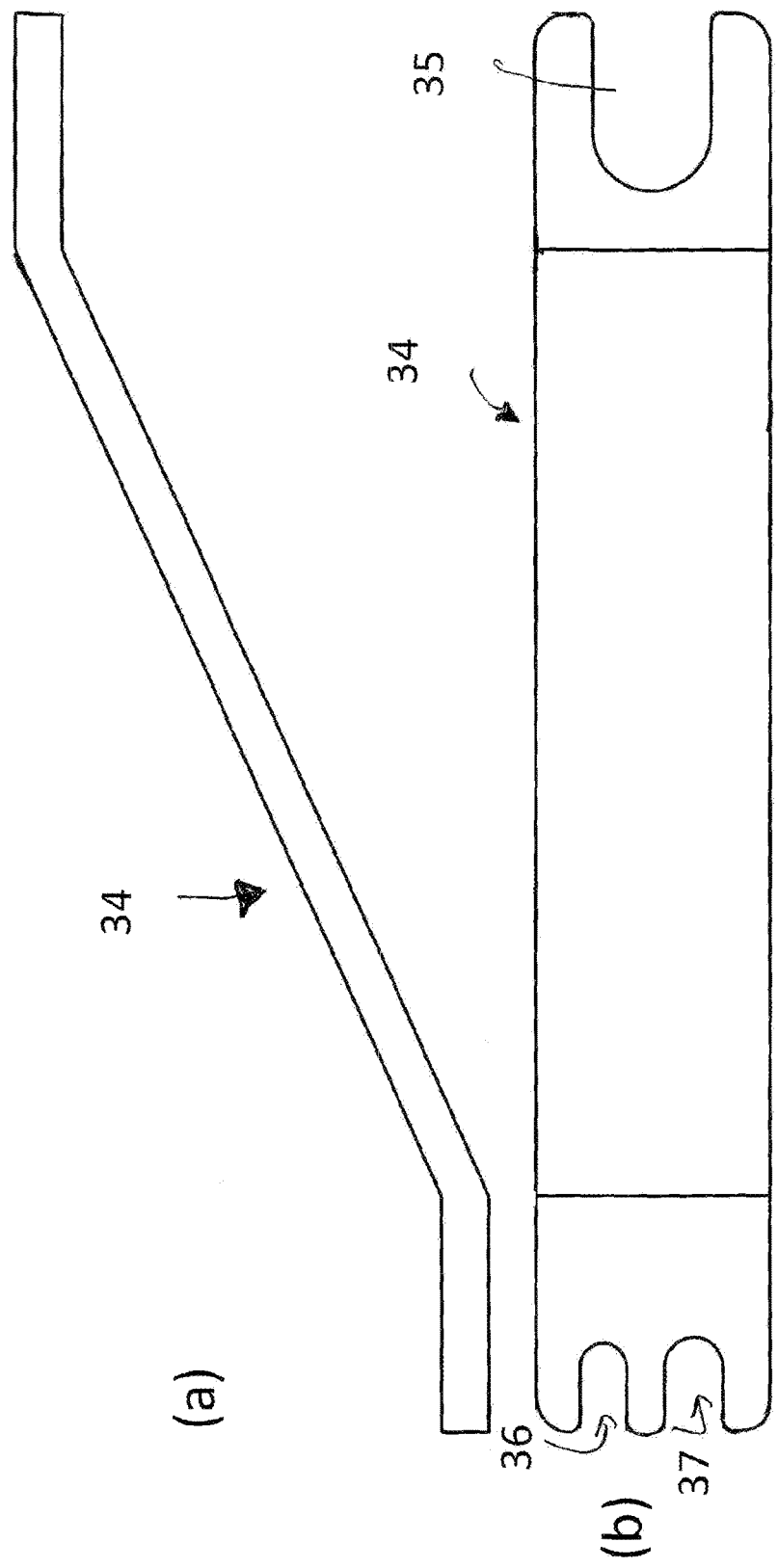
FIG. 8 shows a side view (a) and a plan view (b) of the counter wrench according to the invention.

Finally, FIG. 8 shows a side view according to part (a) and a plan view according to part (b) of FIG. 8 of a counter wrench 34 for use with the guide pin 2 according to the invention, with the socket wrench 4 according to the invention and/or with the drill attachment 31 according to the invention from FIG. 7.

The counter wrench 34 is substantially in the form of a flat bar, which is bent on both outer surfaces by angles which have matching values but which are oriented in opposite directions. An open-end profile 35 is formed in an end portion of the counter wrench 34 in order for it to be placed onto the square profile 27 of the socket wrench 4. On the opposite end portion of the counter wrench 34, an open-end profile 36, 37 is formed in order for it to be placed onto the square portion 22 of the guide pin or in order for it to be placed onto the square outer profile 32 of the drill attachment 31, respectively.

In order to fit the MTV implant 3 according to the invention into the patient's bone, the drill attachment 31 is first screwed to the guide pin 2 by the external thread 23 being screwed into the internal thread 33, in order to produce the assembled tool shown in FIG. 6.

Thereafter, at suitable points on the patient, an incision is made in the skin and the muscle is dissected so that the guide pin 2 can be inserted in the target region. Then the guide pin 2 is then inserted through the skin incision into the patient and is guided through the bone in which the MTV implant 3 is to be anchored, and passes through the skin on the other side of the patient's body. This is carried out using a drilling device, which is brought into an operative connection with the AO shaft 29 of the drill attachment 31.

In this case, the guide pin 2 is guided out of the body on the other side of the body to the extent that at least the square portion 22 of the guide pin 2 is located outside the body. Thereafter, the counter wrench 34 comprising the open-end profile 36 is fitted onto the square portion 22 of the guide pin for the purposes of countering. At the other end of the body, the drill attachment 31 is rotated in order to release the screwed connection between the external thread 23 and the internal thread 33.

Using the guide pin 2 which passes through the body and the bone in which the MTV implant 3 is to be fixed, the MTV implant 3 is then screwed to the proximal end of the guide pin 2 to produce the assembled tool 1 for fitting the implant. For this purpose, a screwed connection is established between the external thread 23 on the guide pin 2 side and the internal thread 8 on the MTV implant 3 side. For this process, a counter wrench 34 is placed onto the square portion 22 of the guide pin 2 in the manner described. On the other side, a counter wrench comprising an open-end profile 35 is fitted onto the square profile 39 of the socket wrench 4.

Once the MTV implant 3 has been screwed to the guide pin 2 by means of the socket wrench 4 in this way, the drill attachment 5 is inserted through the socket wrench 4, and specifically through the inner hole in the socket wrench 4. In addition, the AO shaft 29 of the drill attachment 5 is chucked into the drill chuck of a drilling device. The external thread 28 of the drill attachment 5 is screwed into the internal thread 9 of the MTV implant 3 by rotating the drill attachment 5 until the stop 30 of the drill attachment 5 comes into contact with the proximal end face of the socket wrench 4. The assembled tool 1 shown in FIG. 1 is assembled in this way, the guide pin 2 protruding at least in part in the body and the bone in which the MTV implant 3 is to be anchored.

The MTV implant 3 is now guided into the channel which has been pilot-drilled by the guide pin 2 in the body and the bone by rotating the drill attachment 5 and by means of pressure, and the external fixing thread 11 on the MTV implant 3 side is screwed to the corresponding bone in the patient's body and is fixed to this bone in this way.

Lastly, a socket wrench 34 having the open-end profile 35 is fitted onto the square profile 39 of the socket wrench 4 in order to counter the MTV implant 3 while the drill attachment 5 is unscrewed from the MTV implant 3. In addition, by means of the counter wrench 34 and the corresponding open-end profile 36, the guide pin 2 is unscrewed from the MTV implant 3 which is fixed in the body, the socket wrench 4 and thus the MTV implant 3 being fixed at the same time using a second counter wrench and the open-end profile 35 thereof.

In this way, according to the invention an MTV implant 3, a guide pin 2, a socket wrench 4, a drill attachment 5 and a drill attachment 31 are proposed which make it possible to fix an orthopedic implant for permanent attachment to bones in the bodies of vertebrates and/or humans in a manner which is particularly gentle for the patients.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. An orthopedic implant for permanent attachment to bones in the bodies of vertebrates, comprising:
    an elongate, substantially cylindrical base body with an external fixing thread for screwing into the bone, the base body having a proximal internal thread and a distal internal thread,
    a first connection device having a proximal portion for establishing an operative connection to a drilling device and an external attachment thread that is releasably attached to the proximal internal thread of the base body, and
    a further connection device having, at a distal end, an internal thread complementary to an external thread of a guide device, and at least one counter portion having a non-circular cross-sectional profile.

2. The implant according to claim 1, wherein the external fixing thread is disposed between and remote from the two opposed ends of the cylindrical base body.

3. The implant according to claim 1, wherein the external fixing thread has two complete turns.

4. The implant according to claim 1, wherein the external fixing thread has a greater diameter than the base body.

5. The implant according to claim 1, wherein the base body comprises at least one counter portion having a non-circular cross-sectional profile and arranged between the external fixing thread and the proximal end of the base body.

6. The implant according to claim 5, wherein the base body comprises a conical portion adjoining the counter portion in the direction of a distal end, the conical portion projecting radially beyond the counter portion at an end proximate to the counter portion, and tapers towards the distal end.

7. The implant according to claim 1, wherein the distal internal thread and the proximal internal thread have a corresponding rotational direction.

8. The implant according to claim 1, wherein the external fixing thread is formed in a portion of the base body widened in the manner of a bead.

9. An implant set, comprising
    at least one implant having an elongate, substantially cylindrical base body, a proximal internal thread, a distal internal thread, and an external fixing thread for screwing into bone,
    at least one guide device for pilot-drilling a substantially cylindrical channel, the at least one guide device configured to be releasably attached to the at least one implant, the at least one guide device including an external thread cooperating with the distal internal thread of the at least one implant and at least one counter portion having a non-circular cross-sectional profile,
    at least one counter tool,
    at least one connection device having a portion for establishing an operative connection to a drilling device and an external thread at a distal end releasably attached to the proximal internal thread of the at least one implant,
    wherein the at least one implant cooperates with the at least one guide device, with the at least one counter tool, and with the at least one connection device.

10. The implant set according to claim 9, further comprising a second connection device having at a distal end an internal thread complementary to the external thread of the at least one guide device, and at least one counter portion having a non-circular cross-sectional profile.

* * * * *